(12) United States Patent
Chewter et al.

(10) Patent No.: US 8,747,767 B2
(45) Date of Patent: Jun. 10, 2014

(54) CATALYST RETURN APPARATUS, AND PROCESS FOR REACTING A FEEDSTOCK

(75) Inventors: Leslie Andrew Chewter, Amsterdam (NL); Hubertus Wilhelmus Albertus Dries, Amsterdam (NL); Rene Samson, Amsterdam (NL); Mao Ye, Amsterdam (NL)

(73) Assignee: Shell Oil Company, Houston, TX (US)

( * ) Notice: Subject to any disclaimer, the term of this patent is extended or adjusted under 35 U.S.C. 154(b) by 156 days.

(21) Appl. No.: 13/141,002

(22) PCT Filed: Dec. 21, 2009

(86) PCT No.: PCT/EP2009/067686
§ 371 (c)(1),
(2), (4) Date: Aug. 24, 2011

(87) PCT Pub. No.: WO2010/072733
PCT Pub. Date: Jul. 1, 2010

(65) Prior Publication Data
US 2011/0295049 A1 Dec. 1, 2011

(30) Foreign Application Priority Data
Dec. 22, 2008 (EP) .................................. 08172543

(51) Int. Cl.
*B01J 8/18* (2006.01)
*B01J 8/38* (2006.01)
*B01J 8/00* (2006.01)
*C10G 11/16* (2006.01)

(52) U.S. Cl.
CPC .............. *B01J 8/1863* (2013.01); *B01J 8/1809* (2013.01); *B01J 8/18* (2013.01); *B01J 8/388* (2013.01); *B01J 8/0015* (2013.01); *C10G 11/16* (2013.01); *B01J 2208/00557* (2013.01);
*B01J 2208/00769* (2013.01); *C10G 2300/1081* (2013.01); *C10G 2400/20* (2013.01)
USPC ............ 422/213; 422/110; 422/111; 422/214

(58) Field of Classification Search
CPC .......... B01J 8/18; B01J 8/1809; B01J 8/1863; B01J 8/1881; B01J 8/388; B01J 2208/00769
USPC .......................... 422/110, 111, 145, 213, 214
See application file for complete search history.

(56) References Cited

U.S. PATENT DOCUMENTS 3,785,782 A    1/1974   Cartmell ......................... 23/288
4,379,123 A *  4/1983   Daviduk et al. ............... 422/142
(Continued)

FOREIGN PATENT DOCUMENTS

EP    0145466      6/1985      ............. C10G 11/18
GB    601679       5/1948
(Continued)

OTHER PUBLICATIONS

Weissermehl, et al; "Basic Products of Industrial Syntheses"; Industrial Organic Chemistry; 3rd edition; Wiley, 1997; pp. 13-28.

*Primary Examiner* — Lessanework Seifu

(57) ABSTRACT

A catalyst return apparatus is disclosed as well as a riser reactor system comprising the conduit apparatus and a riser reactor, the conduit apparatus comprising a catalyst return conduit and at least two flow control devices in series, each flow control device arranged to control the flow of fluid through the conduit, wherein the length of the catalyst return conduit is more than 20 m. A process for reacting a feedstock in a riser reactor system comprising a riser reactor, the catalyst return apparatus and, and a stage vessel, the process comprising: holding a fluid comprising the catalyst in the at least one stage vessel for a residence time of at least 10 seconds.

7 Claims, 1 Drawing Sheet

(56) References Cited

U.S. PATENT DOCUMENTS

| | | | |
|---|---|---|---|
| 4,840,928 A * | 6/1989 | Harandi et al. | 502/41 |
| 5,154,818 A | 10/1992 | Harandi et al. | 208/74 |
| 2003/0234209 A1 | 12/2003 | Smith et al. | 208/113 |
| 2004/0076554 A1 | 4/2004 | Kuechler et al. | 422/139 |
| 2006/0096890 A1 | 5/2006 | Pankaj et al. | 208/113 |

FOREIGN PATENT DOCUMENTS

| | | | |
|---|---|---|---|
| WO | WO03008014 | 10/2003 | C10G 11/18 |
| WO | WO2004029178 | 4/2004 | C10G 3/00 |
| WO | WO2005017074 | 2/2005 | C10G 11/00 |
| WO | WO2007135052 | 11/2007 | C07C 2/86 |

* cited by examiner

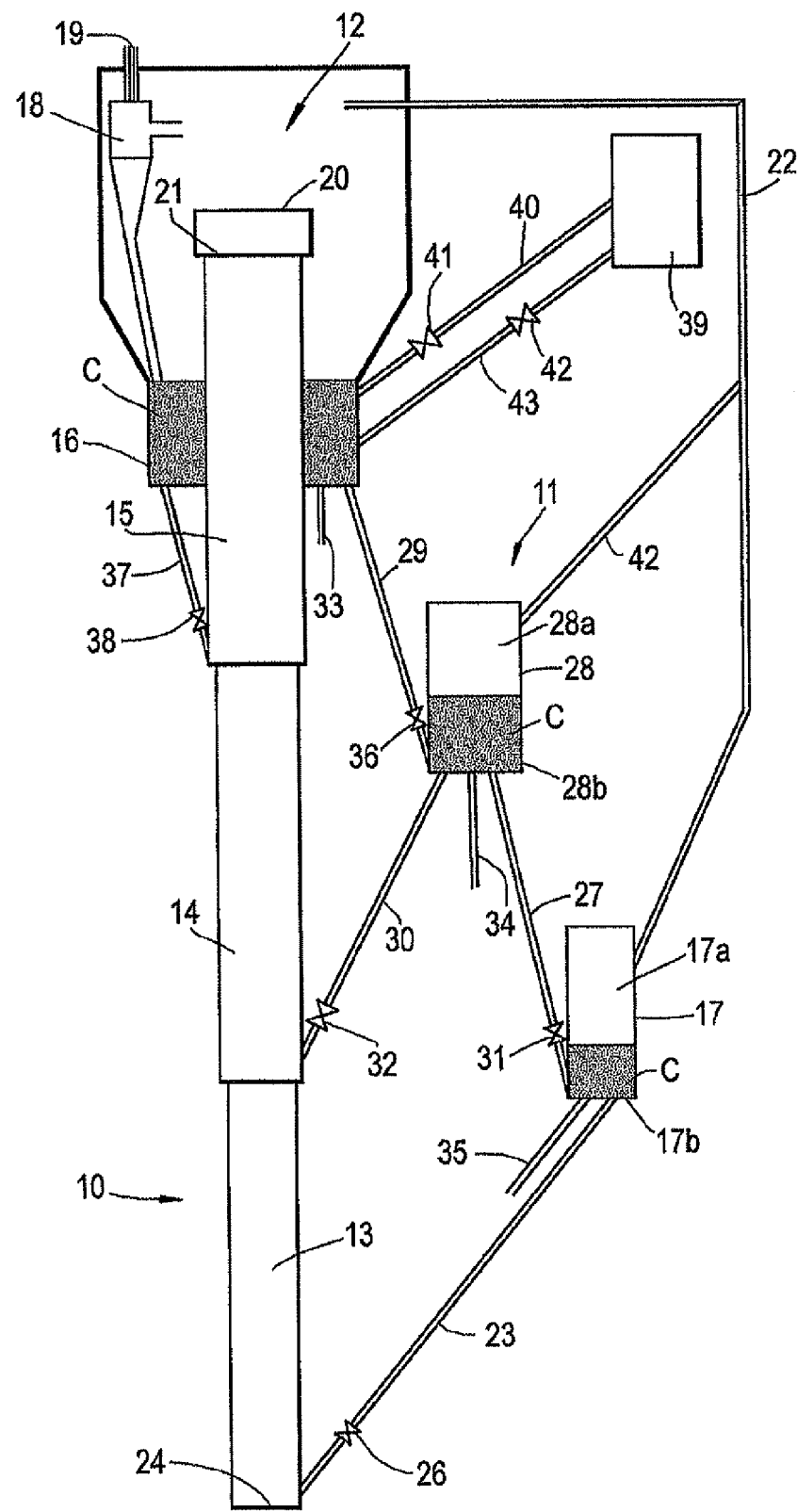

CATALYST RETURN APPARATUS, AND PROCESS FOR REACTING A FEEDSTOCK

PRIORITY CLAIM

The present application claims priority from PCT/EP2009/067686, filed 21 Dec. 2009, which claims priority from European Application 08172543.4, filed 22 Dec. 2008.

BACKGROUND

This invention relates to a riser reactor system, a catalyst return conduit apparatus and a process for reacting a feedstock within the riser reactor system, especially an oxygenate feedstock to produce olefins.

Processes for the preparation of olefins from oxygenates are known in the art. Of particular interest is often the production of light olefins, in particular ethylene and/or propylene. The oxygenate feedstock can for example comprise methanol and/or dimethylether, and an interesting route includes their production from synthesis gas derived from e.g. natural gas or via coal gasification.

For example, WO2007/135052 discloses a process wherein an alcohol and/or ether containing oxygenate feedstock and an olefinic co-feed are reacted in the presence of a zeolite having one-dimensional 10-membered ring channels to prepare an olefinic reaction mixture, and wherein part of the obtained olefinic reaction mixture is recycled as olefinic co-feed. With a methanol and/or dimethylether containing feedstock, and an olefinic co-feed comprising C4 and/or C5 olefins, an olefinic product rich in light olefins can be obtained.

A suitable reactor system for oxygenate-to-olefins reactions includes a riser reactor. Using a riser reactor, a continuous process can be employed where the used catalyst is separated from the product and other fluids in a separation zone, at least some of the catalyst is regenerated to remove some of the coke deposits, and catalyst is reintroduced into the riser reactor via a catalyst return conduit, also referred to as a standpipe. It is important for smooth continuous operation of a riser reactor system that the solids circulation operates well.

US2003/0234209 teaches a method for controlling solids circulation in a gas/solids reaction system. The method entails aerating solid particles in a standpipe, wherein aeration fluid is injected into the standpipe away from the internal wall.

In the design of riser reactor systems, e.g. for oxygenate-to-olefins conversions, it can be desirable to use tall reactors, in order to provide the right reactions conditions in terms of catalyst concentration, superficial velocity, flow regime and/or residence time for a given cross-sectional area of the riser. For commercially interesting throughputs and a desired height aspect ratio between height and cross-sectional area, reactors can be desired to reach heights of 30 m, 50 m, 70 m or even more.

US2004/0076554 addresses a particular problem encountered when designing a reactor system so tall, namely that heavy equipment at the top of such a structure requires expensive support structures. US2004/0076554 discloses a multiple riser reactor, wherein the effluent from risers is laterally fed into a common separation vessel, which is arranged between the riser reactors and not on above them. From the lower end of the separation vessel catalyst guided via a central downcomer to a catalyst retention zone, and from the catalyst retention zone short standpipes feed the catalyst back to the inlets of the multiple risers. In this way the overall height of the structure is reduced.

Applicant has realized another problem in designing tall riser reactors, in particular when a design is used in which a catalyst retention zone, wherein catalyst is collected after separation and perhaps regeneration, is arranged at a very high position, e.g. at the top of a tall riser reactor. In this case the standpipe for feeding catalyst from the catalyst retention zone to the lower end of the riser becomes very tall as well. Applicant has realized that it is problematic to reliably control the flow of fluid in such a standpipe of more than 20 meters height, since valves that are typically used, e.g. slide valves, cannot be used at higher pressure differences than about 1 bar. Otherwise wear would be too high and control unreliable.

There is a need for an improved catalyst return in riser reactors.

SUMMARY OF THE INVENTION

According to a first aspect of the invention, there is provided a catalyst return apparatus suitable for use in a riser reactor system, the apparatus comprising a catalyst return conduit and at least two flow control devices in series, wherein the length of the catalyst return conduit is more than 20 m. Each flow control device is arranged to control the flow of fluid through the catalyst return conduit. The expression 'catalyst return conduit' is user herein to denote a flowpath for catalyst from a catalyst retention zone such as a collector vessel to an inlet of a riser reactor. The conduit can be formed of various sections and elements that are in fluid communication. The catalyst return conduit serves to return at least the larger part of the catalyst to the reactor. Therefore, preferably, the catalyst return conduit does not comprise or incorporate regeneration or heat exchange units, as such units may put limitations on the catalyst throughput. Reference, herein to heat exchangers is to units that would change the temperature of the catalyst to an extent beyond the temperature change, occurring while the catalyst is passed through the catalyst return conduit without additional heat exchange.

DETAILED DESCRIPTION OF THE INVENTION

By providing at least two flow control devices, such as valves, in series, the height can be broken down in several portions, wherein each of the valves only has to handle a portion of the overall pressure drop. In this way the pressure drop per valve can e.g. be limited to about 1 bar or below.

The flow control devices are typically valves, and will in the description be referred to as valves for simplicity. The valves are normally spaced apart by at least 5 m and preferably at least 10 m. Preferably at least one flow control device is present at least every 20 m along the catalyst return apparatus.

The apparatus may further comprise a means to reconstitute catalyst flow. Such means to reconstitute catalyst flow can in particular be a stage vessel. The stage vessel has suitably a width at least twice a width of the conduit. Typically the or each stage vessel has a width of at least three, preferably at least four, times a width of the conduit. In use the stage vessel allows the returning fluidised catalyst to separate into a predominantly gas phase above a predominantly fluidised solid phase. From the fluidized solid phase, a well-defined flow of catalyst into a following section or portion of the flowpath along the catalyst return apparatus can start. The predominantly gas phase can have more than 70 vol % gas, preferably more than 80 vol %. It will be clear that depending on the throughput the separation between the two phases may not be very sharp and that there may be a gradient of decreasing density from bottom to top, but solids will settle at the bottom and form a fluidize bed there. The predominantly fluidised solid phase can have more than 40 vol % solid, preferably more than 50 vol % solid.

Normally the stage vessel comprises a gas inlet to further fluidise the catalyst during use.

Preferably the catalyst return conduit comprises at least one stage vessel at least every 20 m.

Preferably at least one flow control device, such as a valve, is provided for the or each stage vessel, typically within 1 m upstream of the or each stage vessel, to control the fluid within the conduit at that point. Typically the stage vessel is located between two valves.

The conduit may comprise a first portion above the stage vessel and a second portion below the stage vessel, and further portions between stage vessels if more than one stage vessels is provided. The first and second portions and/or other portions are typically not co-linear. Each portion of standpipe (conduit) may be at least 4 m in length.

The invention also provides a riser reactor system comprising a catalyst return apparatus as described herein and a riser reactor.

The apparatus typically comprises at least one stage vessel, as described herein.

The riser reactor system may comprise a pressure equalisation means to equalise the gas pressure in the stage vessel(s) with the gas pressure at the top of the riser reactor, especially with a separation zone provided at the top of the riser reactor. For example a further conduit may be provided to connect the gas phase of the stage vessel(s) with the gas phase at the top of the riser reactor.

The invention also provides a process for reacting a feedstock in a riser reactor system with a catalyst return conduit according to the invention and at least one stage vessel, the process comprising holding a fluidised catalyst in the at least one stage vessel for a residence time of at least 10 seconds, preferably at least 20 seconds.

The residence time may be determined by calculations based on the input and output rate. The residence time can be defined as the average amount of catalyst in the stage vessel divided by the average flow of catalyst (in terms of amount per unit of time). The amount can for example be measured as a mass. The process of holding fluid within the stage vessel is very typically a continuous process rather than a batch process.

In the simplest embodiment of the riser reactor system, the riser reactor has a constant cross-sectional area. As riser reactors normally have circular cross-sections, their cross-sectional area is proportional to their diameter.

In a preferred embodiment, the riser reactor system comprises two or more serially arranged riser reactor stages, wherein each riser reactor stage comprises a single riser reactor segment or a plurality of parallel riser reactors.

The applicant has found that selectivity of an oxygenate conversion process towards desired olefins, in particular ethylene, can be significantly improved using a serial riser reactor system, in which oxygenate feedstock together with fluidised catalyst is stagewise added to a plurality of the riser reactor stages, in particular to the first and at least one additional riser reactor stage.

Preferably each stage comprises a single riser reactor segment. Preferably therefore the riser reactor system comprises a plurality of riser reactor segments.

In a particular embodiment, riser stages may be arranged by stacking riser segments on top of each other such that they are co-linear and so fluidised catalyst may flow up the lower riser of the first stage and then continue up the upper riser of a subsequent stage. Such a stacked arrangement normally leads to a substantial overall height of the reactor system, such as more than 20 m, more than 30 m, or more than 40 m, and so increases the benefit of the catalyst return conduit in accordance with the present invention.

Preferably in such an embodiment a further catalyst return conduit is provided to connect to a further catalyst inlet of a consecutive stage above the catalyst inlet of the first stage. This further catalyst inlet is typically at least 5 m from the bottom of the riser reactor system.

Between 2 and 10, preferably between 2 and 5, more preferably three or four, riser reactor stages, such as riser segments can be provided.

Preferably the first of the two or more serially arranged riser reactor stages has a smaller total cross-sectional area than at least one of the subsequent riser reactor stages. It is particularly beneficial if the total cross-sectional area of each subsequent riser reactor stage, after the first, is higher than that of the preceding riser reactor stage. The total cross-sectional area is the sum of the cross-sectional areas of all riser reactors in a particular stage. In preferred embodiments when there is only one riser reactor segment in a stage, its cross-section defines the total cross-sectional area of that stage. Increasing the cross-sectional area can partly or fully compensate for the increase in volumetric flow rate due to additional catalyst (and optionally feedstock), so that the flow velocity in the riser does not increase beyond critical values impeding for example conversion, catalyst stability and/or attrition.

The invention also provides a process for the preparation of an olefinic product within a riser reactor system as described herein, the process comprising reacting an oxygenate feedstock in the presence of an oxygenate conversion catalyst under oxygenate-to-olefin conversion conditions in the riser reactor system, to obtain the olefinic product.

Typically in use the oxygenate feedstock is contacted with an oxygenate conversion catalyst to obtain a riser reactor effluent from each stage and at least part of the riser reactor effluent of a preceding riser reactor stage is fed into a subsequent riser reactor stage, and preferably fluidised catalyst and optionally oxygenate is added to a plurality of the riser reactor stages.

The riser reactor effluent of a preceding riser reactor stage comprises gaseous effluent and solid oxygenate conversion catalyst. Normally, at least 50 wt % of the gaseous effluent is fed to the subsequent riser reactor stage, in particular at least 80%, more in particular at least 90%. Further, it can be beneficial not to separate solids and gases between subsequent riser reactor stages. So, normally also at least 50 wt % of the solid oxygenate conversion catalyst is fed to the subsequent riser reactor stage, in particular at least 80%, more in particular at least 90%. More in particular, substantially all riser reactor effluent from one riser reactor stage can be fed to the subsequent riser reactor stage.

The oxygenate feedstock suitably comprises oxygenate species having an oxygen-bonded methyl group, such as methanol or dimethylether. Preferably the oxygenate feedstock comprises at least 50 wt % of methanol and/or dimethylether, more preferably at least 80 wt %, most preferably at least 90 wt %.

The oxygenate feedstock can be obtained from a different or separate reactor, which converts methanol at least partially into dimethylether and water. Water may be removed by e.g. distillation. In this way, water is present in the process of converting oxygenate to olefins, which has advantages for the process design and lowers the severity of hydrothermal conditions the catalyst is exposed to.

The oxygenate feedstock can comprise an amount of water, preferably less than 10 wt %, more preferably less than 5 wt %. Preferably the oxygenate feedstock contains essentially no hydrocarbons other than oxygenates, i.e. less than 5 wt %, preferably less than 1 wt %.

In one embodiment, the oxygenate is obtained as a reaction product of synthesis gas. Synthesis gas can for example be generated from fossil fuels, such as from natural gas or oil, or from the gasification of coal. Suitable processes for this purpose are for example discussed in Industrial Organic Chemistry, Klaus Weissermehl and Hans-Jürgen Arpe, 3rd edition, Wiley, 1997, pages 13-28. This book also describes the manufacture of methanol from synthesis gas on pages 28-30.

In another embodiment the oxygenate is obtained from biomaterials, such as through fermentation. For example by a process as described in DE-A-10043644.

In one embodiment, oxygenate is added to each of the riser reactor stages. Preferably the oxygenate added at the different stages is derived from a common oxygenate feedstock source. The common oxygenate feedstock source can for example be a storage vessel, feed line, or a different or separate reactor. In this way oxygenate comprising feedstock of substantially the same composition is fed to and converted in each of the riser reactor stages.

In one embodiment, the mass flow rate of oxygenate conversion catalyst in each subsequent riser reactor stage, after the first, to which oxygenate is added is higher than in the preceding riser reactor stage. Thus, the addition of fresh oxygenate feed is accommodated by additional oxygenate conversion catalyst. In this way the weight hourly space velocity (WHSV), defined as the throughput of the weight of reactants and reaction products per hour, and per weight of catalyst in the reactor, can be maintained above a selected minimum value, in order to achieve sufficient conversion.

Preferably the oxygenate feedstock is reacted to produce the olefinic product in the presence of an olefinic co-feed. By an olefinic composition or stream, such as an olefinic product, product fraction, fraction, effluent, reaction effluent or the like is understood a composition or stream comprising one or more olefins, unless specifically indicated otherwise. Other species can be present as well. Apart from olefins, the olefinic co-feed may contain other hydrocarbon compounds, such as for example paraffinic compounds. Preferably the olefinic co-feed comprises an olefinic portion of more than 50 wt %, more preferably more than 60 wt %, still more preferably more than 70 wt %, which olefinic portion consists of olefin(s). The olefinic co-feed can also consist essentially of olefin(s).

Any non-olefinic compounds in the olefinic co-feed are preferably paraffinic compounds. Such paraffinic compounds are preferably present in an amount in the range of from 0 to 50 wt %, more preferably in the range of from 0 to 40 wt %, still more preferably in the range of from 0 to 30 wt %.

By an olefin is understood an organic compound containing at least two carbon atoms connected by a double bond. The olefin can be a mono-olefin, having one double bond, or a poly-olefin, having two or more double bonds. Preferably olefins present in the olefinic co-feed are mono-olefins. C4 olefins, also referred to as butenes (1-butene, 2-butene, iso-butene, and/or butadiene), in particular C4 mono-olefins, are preferred components in the olefinic co-feed.

Preferably the olefinic co-feed is at least partially obtained by a recycle stream formed by recycling a suitable fraction of the reaction product comprising C4 olefin. The skilled artisan knows how to obtain such fractions from the olefinic reaction effluent such as by distillation.

In one embodiment at least 70 wt % of the olefinic co-feed, during normal operation, is formed by the recycle stream, preferably at least 90 wt %, more preferably at least 99 wt %. Most preferably the olefinic co-feed is during normal operation formed by the recycle stream, so that the process converts oxygenate feedstock to predominantly light olefins without the need for an external olefins stream. During normal operation means for example in the course of a continuous operation of the process, for at least 70% of the time on stream. The olefinic co-feed may need to be obtained from an external source, such as from a catalytic cracking unit or from a naphtha cracker, during start-up of the process, when the reaction effluent comprises no or insufficient C4+ olefins.

A particularly preferred olefinic recycle stream is a C4 fraction containing C4 olefin(s), but which can also contain a significant amount of other C4 hydrocarbon species, in particular C4 paraffins, because it is difficult to economically separate C4 olefins and paraffins, such as by distillation.

In a preferred embodiment the olefinic co-feed and preferably also the recycle stream comprises C4 olefins and less than 10 wt % of C5+ hydrocarbon species, more preferably at least 50 wt % of C4 olefins, and at least a total of 70 wt % of C4 hydrocarbon species.

The olefinic co-feed and preferably also the recycle stream, can in particular contain at least a total of 90 wt % of C4 hydrocarbon species. In a preferred embodiment, the olefinic co-feed comprises less than 5 wt % of C5+ olefins, preferably less than 2 wt % of C5+ olefins, even more preferably less than 1 wt % of C5+ olefins, and likewise the recycle stream. In another preferred embodiment, the olefinic co-feed, comprises less than 5 wt % of C5+ hydrocarbon species, preferably less than 2 wt % of C5+ hydrocarbon species even more preferably less than 1 wt % of C5+ hydrocarbon species, and likewise the recycle stream.

Thus in certain preferred embodiments, the olefinic portion of the olefinic co-feed, and of the recycle stream, comprises at least 90 wt % of C4 olefins, more preferably at least 99 wt %. Butenes as co-feed have been found to be particularly beneficial for high ethylene selectivity. Therefore one particularly suitable recycle stream consists essentially, i.e. for at least 99 wt %, of 1-butene, 2-butene (cis and trans), isobutene, n-butane, isobutane, butadiene.

In certain embodiments, the recycle stream can also comprise propylene. This may be preferred when a particularly high production of ethylene is desired, so that part or all of the propylene, such as at least 5 wt % thereof, produced is recycled together with C4 olefins.

The preferred molar ratio of oxygenate in the oxygenate feedstock to olefin in the olefinic co-feed depends on the specific oxygenate used and the number of reactive oxygen-bonded alkyl groups therein. Preferably the molar ratio of oxygenate to olefin in the total feed lies in the range of 10:1 to 1:10, more preferably in the range of 5:1 to 1:5 and still more preferably in the range of 3:1 to 1:3.

In a preferred embodiment wherein the oxygenate comprises only one oxygen-bonded methyl group, such as methanol, the molar ratio preferably lies in the range of from 5:1 to 1:5 and more preferably in the range of 2.5:1 to 1:2.5.

In another preferred embodiment wherein the oxygenate comprises two oxygen-bonded methyl groups, such as for example dimethylether, the molar ratio preferably lies in the range of from 5:2 to 1:10 and more preferably in the range of 2:1 to 1:4. Most preferably the molar ratio in such a case is in the range of 1.5:1 to 1:3.

The process to prepare an olefin is typically carried out in presence of a molecular sieve having one-dimensional 10-membered ring channels. These are understood to be molecular sieves having only 10-membered ring channels in one direction which are not intersected by other 8, 10 or 12-membered ring channels from another direction.

Preferably, the molecular sieve is selected from the group of TON-type (for example zeolite ZSM-22), MTT-type (for example zeolite ZSM-23), STF-type (for example SSZ-35), SFF-type (for example SSZ-44), EUO-type (for example ZSM-50), and EU-2-type molecular sieves or mixtures thereof.

MTT-type catalysts are more particularly described in e.g. U.S. Pat. No. 4,076,842. For purposes of the present invention, MTT is considered to include its isotypes, e.g., ZSM-23, EU-13, ISI-4 and KZ-1.

TON-type molecular sieves are more particularly described in e.g. U.S. Pat. No. 4,556,477. For purposes of the present invention, TON is considered to include its isotypes, e.g., ZSM-22, Theta-1, ISI-1, KZ-2 and NU-10.

EU-2-type molecular sieves are more particularly described in e.g. U.S. Pat. No. 4,397,827. For purposes of the present invention, EU-2 is considered to include its isotypes, e.g., ZSM-48.

In a further preferred embodiment a molecular sieve of the MTT-type, such as ZSM-23, and/or a TON-type, such as ZSM-22 is used.

Molecular sieve and zeolite types are for example defined in Ch. Baerlocher and L. B. McCusker, Database of Zeolite Structures: http://www.iza-structure.org/databases/, which database was designed and implemented on behalf of the Structure Commission of the International Zeolite Association (IZA-SC), and based on the data of the 4th edition of the Atlas of Zeolite Structure Types (W. M. Meier, D. H. Olson and Ch. Baerlocher). The *Atlas of Zeolite Framework Types*, 5th revised edition 2001 and 6$^{th}$ edition 2007 may also be consulted.

Preferably, molecular sieves in the hydrogen form are used in the oxygenate conversion catalyst, e.g., HZSM-22, HZSM-23, and HZSM-48, HZSM-5. Preferably at least 50% w/w, more preferably at least 90% w/w, still more preferably at least 95% w/w and most preferably 100% of the total amount of molecular sieve used is in the hydrogen form. When the molecular sieves are prepared in the presence of organic cations the molecular sieve may be activated by heating in an inert or oxidative atmosphere to remove organic cations, for example, by heating at a temperature over 500° C. for 1 hour or more. The zeolite is typically obtained in the sodium or potassium form. The hydrogen form can then be obtained by an ion exchange procedure with ammonium salts followed by another heat treatment, for example in an inert or oxidative atmosphere at a temperature over 300° C. The molecular sieves obtained after ion-exchange are also referred to as being in the ammonium form.

Preferably the molecular sieve having one-dimensional 10-membered ring channels has a silica to alumina ratio (SAR) in the range of from 1 to 500, preferably in the range of from 10 to 200. The SAR is defined as the molar ratio of $SiO_2/Al_2O_3$ corresponding to the composition of the molecular sieve.

For ZSM-22, a SAR in the range of 40-150 is preferred, in particular in the range of 70-120. Good performance in terms of activity and selectivity has been observed with a SAR of about 100.

For ZSM-23, an SAR in the range of 20-120 is preferred, in particular in the range of 30-80. Good performance in terms of activity and selectivity has been observed with a SAR of about 50.

In a special embodiment the reaction is performed in the presence of a more-dimensional molecular sieve, such as ZSM-5. Suitably to this end the oxygenate conversion catalyst comprises at least 1 wt %, based on total molecular sieve in the oxygenate conversion catalyst, of a further molecular sieve having more-dimensional channels, in particular at least 5 wt %, more in particular at least 8 wt %.

The further molecular sieve having more-dimensional channels is understood to have intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably the channels in at least one of the directions are 10-membered ring channels. The further molecular sieve can be for example a FER type zeolite which is a two-dimensional structure and has 8- and 10-membered rings intersecting each other. Preferably however the intersecting channels in the further molecular sieve are each 10-membered ring channels. Thus the further molecular sieve may be a zeolite, or a SAPO-type (silicoaluminophosphate) molecular sieve. More preferably however the further molecular sieve is a zeolite. A preferred further molecular sieve is an MFI-type zeolite, in particular zeolite ZSM-5.

The presence of the further molecular sieve in the oxygenate conversion catalyst was found to improve stability (slower deactivation during extended runs) and hydrothermal stability compared to a catalyst with only the one-dimensional molecular sieve and without the more-dimensional molecular sieve. Without wishing to be bound by a particular hypothesis or theory, it is presently believed that this is due to the possibility for converting larger molecules by the further molecular sieve having more-dimensional channels, that were produced by the first molecular sieve having one-dimensional 10-membered ring channels, and which would otherwise form coke. When the one-dimensional aluminosiclicate and the more-dimensional molecular sieve are formulated such that they are present in the same catalyst particle, such as in a spray-dried particle, this intimate mix was found to improve the selectivity towards ethylene and propylene, more in particular towards ethylene.

The weight ratio between the molecular sieve having one-dimensional 10-membered ring channels, and the further molecular sieve having more-dimensional channels can be in the range of from 1:100 to 100:1, preferably 1:1 to 100:1, more preferably in the range of 9:1 to 2:1.

Preferably the further molecular sieve is an MFI-type molecular sieve, in particular zeolite ZSM-5, having a silica to alumina ratio (SAR) of at least 60, more preferably at least 80, even more preferably at least 100, yet more preferably at least 150. At higher SAR the percentage of C4 saturates in the C4 totals produced is minimized. In special embodiments the oxygenate conversion catalyst can comprise less than 35 wt % of the further molecular sieve, based on the total molecular sieve in the oxygenate conversion catalyst, in particular less than 20 wt %, more in particular less than 18 wt %, still more in particular less than 15 wt %.

In one embodiment the oxygenate conversion catalyst can comprise more than 50 wt %, at least 65 wt %, based on total molecular sieve in the oxygenate conversion catalyst, of the molecular sieve having one-dimensional 10-membered ring channels. The presence of a majority of such molecular sieve strongly determines the predominant reaction pathway.

The molecular sieve can be used as such or in a formulation, such as in a mixture or combination with a so-called binder material and/or a filler material, and optionally also with an active matrix component. Other components can also be present in the formulation. If one or more molecular sieves are used as such, in particular when no binder, filler, or active matrix material is used, the molecular sieve itself is/are referred to as oxygenate conversion catalyst. In a formulation, the molecular sieve in combination with the other components of the mixture such as binder and/or filler material is/are referred to as oxygenate conversion catalyst.

It is desirable to provide a catalyst having good mechanical or crush strength, because in an industrial environment the catalyst is often subjected to rough handling, which tends to break down the catalyst into powder-like material. The latter causes problems in the processing. Preferably the molecular sieve is therefore incorporated in a binder material. Examples of suitable materials in a formulation include active and inactive materials and synthetic or naturally occurring zeolites as well as inorganic materials such as clays, silica, alumina, silica-alumina, titania, zirconia and aluminosilicate. For present purposes, inert materials, such as silica, are preferred because they may prevent unwanted side reactions which may take place in case a more acidic material, such as alumina or silica-alumina is used.

In one embodiment the oxygenate added can be used for temperature control, and to this end the temperature of the oxygenate added to at least one of the riser reactors of any one of the riser reactor stages is set in dependence of a predetermined desired temperature in this riser reactor. For example, depending on the temperature and mass flow rate of the effluent stream from the previous riser reactor, the temperature and mass flow rate of additional catalyst, the temperature of the oxygenate can be set, e.g. by heat exchange, so that near the inlet of the riser reactor a predetermined inlet temperature of the mixture of the various feeds is realized.

In one embodiment, each gaseous effluent from one of the riser reactors has an oxygenate concentration below 10 wt %, in particular below 5 wt %, preferably below 2 wt %, more preferably below 1 wt %, still more preferably below 0.1 wt %. In this way, substantially full conversion of oxygenate in each riser reactor is realized. This is particularly beneficial at the last reactor effluent, as otherwise unreacted oxygenate has to be separated from the effluent in a work-up section. Separating e.g. unreacted methanol from water formed in the process is an undesirable and costly step in an industrial process.

The reaction to produce the olefins can be carried out over a wide range of temperatures and pressures. Suitably, however, the oxygenate feed and olefinic co-feed are contacted with the molecular sieve at a temperature in the range of from 200° C. to 650° C. In a further preferred embodiment the temperature is in the range of from 250° C. to 600° C., more preferably in the range of from 300° C. to 550° C., most preferably in the range of from 450° C. to 550° C. Preferably the reaction to produce the olefins is conducted at a temperature of more than 450° C., preferably at a temperature of 460° C. or higher, more preferably at a temperature of 490° C. or higher. At higher temperatures a higher activity and ethylene selectivity is observed. Molecular sieves having one-dimensional 10-membered ring channels can be operated under oxygenate conversion conditions at such high temperatures with acceptable deactivation due to coking, contrary to molecular sieves with smaller pores or channels, such as 8-membered ring channels. Temperatures referred to hereinabove represent reaction temperatures, and it will be understood that a reaction temperature can be an average of temperatures of various feed streams and the catalyst in the reaction zone.

In addition to the oxygenate, and the olefinic co-feed, a diluent may be fed into the reactor system. It is preferred to operate without a diluent, or with a minimum amount of diluent, such as less than 200 wt % of diluent based on the total amount of oxygenate feed, in particular less than 100 wt %, more in particular less than 20 wt %. Any diluent known by the skilled person to be suitable for such purpose can be used. Such diluent can for example be a paraffinic compound or mixture of compounds. Preferably, however, the diluent is an inert gas. The diluent can be argon, nitrogen, and/or steam. Of these, steam is the most preferred diluent. For example, the oxygenate feed and optionally olefinic co-feed can be diluted with steam, for example in the range of from 0.01 to 10 kg steam per kg oxygenate feed. In one embodiment small amounts of water are added in order to improve the stability of the catalyst by reducing coke formation.

In one embodiment, each gaseous effluent from one of the riser reactor stages, or preferably from all riser reactors individually, has a concentration of C5+ olefins (pentenes and higher olefins) of below 10 wt %, preferably below 5 wt %, more preferably below 2 wt %, yet more preferably below 1 wt %, still more preferably below 0.1 wt %. In particular, the C5+ olefins can comprise at least 50 wt % pentenes, more in particular at least 80 wt %, even more in particular at least 90 wt % of pentenes. In particular the pentene concentration of the gaseous effluent can be below 10 wt %, preferably below 5 wt %, more preferably below 2 wt %, yet more preferably below 1 wt %, still more preferably below 0.1 wt %.

In this way the ratio of C5+ olefins (in particular C5 olefins) to oxygenate at the subsequent riser inlet to which oxygenate is added is kept minimum in the process. Without wishing to be bound to a particular hypothesis, it is currently believed that keeping the ratio C5+ olefins/oxygenate, in particular C5 olefins/oxygenate, small is beneficial to ethylene selectivity, more in particular in the case that the oxygenate comprises oxygen-bonded methyl groups. It is currently believed that pentenes should be preferentially cracked to yield ethylene and propylene, as opposed to alkylation to higher olefins by reaction with the oxygenate. Cracking of higher olefins is thought to result is a lower concentration of ethylene in the final product.

The olefinic product or reaction effluent is typically fractionated. The skilled artisan knows how to separate a mixture of hydrocarbons into various fractions, and how to work up fractions further for desired properties and composition for further use. The separations can be carried out by any method known to the skilled person in the art to be suitable for this purpose, for example by vapour-liquid separation (e.g. flashing), distillation, extraction, membrane separation or a combination of such methods. Preferably the separations are carried out by means of distillation. It is within the skill of the artisan to determine the correct conditions in a fractionation column to arrive at such a separation. He may choose the correct conditions based on, inter alia, fractionation temperature, pressure, trays, reflux and reboiler ratios.

At least a light olefinic fraction comprising ethylene and a heavier olefinic fraction comprising C4 olefins and less than 10 wt % of C5+ hydrocarbon species are normally obtained. Preferably also a water-rich fraction is obtained. Also a lighter fraction comprising methane, carbon monoxide, and/or carbon dioxide can be obtained, as well as one or more heavy fractions comprising C5+ hydrocarbons. Such heavy fraction can for example be used as gasoline blending component.

In the process also a significant amount of propylene is normally produced. The propylene can form part of the light olefinic fraction comprising ethene, and which can suitably be further fractionated into various product components. Propylene can also form part of the heavier olefinic fraction comprising C4 olefins. The various fractions and streams referred to herein, in particular the recycle stream, can be obtained by fractionating in various stages, and also by blending streams obtained during the fractionation. Typically, an ethylene and a propylene stream of predetermined purity such as pipeline grade, polymer grade, chemical grade or export quality will be obtained from the process, and also a stream rich in C4 comprising C4 olefins and optionally C4 paraffins. In a preferred embodiment the process according to the invention is designed to produce lower olefins for recovery and onward processing and/or sale. Typically therefore, a stream comprising at least 50 wt %, preferably at least 75 wt %, C2 to C3 olefins (ethylene and/or propylene) is separated from the reaction product, based on total reaction product.

It shall be clear that the heavier olefinic fraction comprising C4 olefins, forming the recycle stream, can be composed from quantities of various fractionation streams. So, for example, some amount of a propylene-rich stream can be blended into a C4 olefin-rich stream. In a particular embodiment at least 90 wt % of the heavier olefinic fraction comprising C4 olefins can be formed by the overhead stream from a debutaniser column receiving the bottom stream from a depropanizer column at their inlet, more in particular at least 99 wt % or substantially all.

Suitably the olefinic reaction effluent comprises less than 10 wt %, preferably less than 5 wt %, more preferably less than 1 wt %, of C6-C8 aromatics. Producing low amounts of aromatics is desired since any production of aromatics consumes oxygenate which is therefore not converted to lower olefins.

The process may be started up by using olefins obtained from an external source for the olefinic co-feed, if used. Such olefins may for example be obtained from a steam cracker, a catalytic cracker, alkane dehydrogenation (e.g. propane or butane dehydrogenation). Further, such olefins can be bought from the market.

When a molecular sieve having more-dimensional channels such as ZSM-5 is present in the oxygenate conversion catalyst, even in minority compared to the molecular sieve having one-dimensional 10-membered ring channels, start up is possible without an olefinic co-feed from an external source. ZSM-5 for example is able to convert an oxygenate to an olefin-containing product, so that a recycle can be established.

Typically the oxygenate conversion catalyst deactivates in the course of the process. Conventional catalyst regeneration techniques can be employed, such as oxidation of coke in a regenerator. The molecular sieve having one-dimensional 10-membered ring channels used in the process of the present invention can have any shape known to the skilled person to be suitable for this purpose, for it can be present in the form of spray-dried particles, spheres, tablets, rings, extrudates, etc. Extruded catalysts can be applied in various shapes, such as, cylinders and trilobes. Spray-dried particles are preferred.

An embodiment of the present invention will now be described by way of example only and with reference to and as shown in FIG. 1, which is a front diagrammatic view of a catalyst return apparatus and riser reactor system in accordance with the present invention.

FIG. 1 shows a riser reactor system 10 comprising a first riser segment 13, a second riser segment 14 and a third riser segment 15. The riser segments 13-15 are stacked such that they are co-linear so that fluid together with catalyst particles may travel up sequentially from the first riser 13 through the second riser 14 to the third riser 15. The riser reactor system can be more than 40 meters high.

As described in more detail below, catalyst particles are separated from the gaseous reaction products in a separation zone 12 and recovered in a collection vessel or catalyst retention zone 16 at the top of the third riser segment 15. Catalyst C from the catalyst retention zone is returned by the catalyst return apparatus 11 to the catalyst inlets at the bottom of the three riser segments. The flowpath to the bottom of the first riser includes (in sequence) a conduit 29, a first stage vessel 28, a further conduit 27, a second stage vessel 17 and a final conduit 23.

Valves 36, 31 are provided to control fluid flow in the conduits 29 and 27, immediately upstream of the stage vessels 28, 17; and a third valve 26 controls fluid flow in the conduit 23 immediately upstream of the first riser 13.

When fluidized catalyst flows down a standpipe for a significant length, the flow regime is difficult to control, in particular when a valve was passed. The stage vessels allow the fluidized catalyst flow on the way to the bottom of the riser to settle into a gas phase 17a, 28a, and a fluidized solid phase 17b, 28b. From the fluidized solid phase in the stage vessel a well-defined flow into the subsequent section of the flowpath starts. In this way the stage vessels serve to reconstitute catalyst flow.

The stage vessels 28 and 17 also have a much greater width than the conduits and are typically at least 2 m in width and at least 3 m in height whereas the conduits can typically be 0.5 m-1 m in width. The stage vessels suitably comprise gas inlets 34, 35 for the fluidisation of catalyst 11 during use. The stage vessels are also pressure balanced with each other and the riser reactor system 10 via conduits 22 and 42.

Thus catalyst particles recovered from the top of the third riser 15 are transported via the conduits 29, 27, 23 and stage vessels 17, 28 to the bottom of the first riser 13.

The presence of valves on the conduits and additionally also the stage vessels allows the pressure difference between the catalyst retention zone 16 at the top of the riser reactor system, and the catalyst inlet at the bottom of the riser reactor system 10, which can for example be 2 bar or more, to be handled well, allowing reliable catalyst recirculation while observing the optimum operation window for the pressure difference over a valve of say maximum 1 bar.

The riser reactor system is especially useful for the catalytic conversion of oxygenates to olefins, especially C2 and C3 olefins.

Further features of the riser reactor system 10 and catalyst return apparatus 11 will now be described. As shown in FIG. 1, a riser end device 20 is connected to a top end 21 of the third riser segment 15 to improve separation of the catalyst from the reactor effluent from the third riser segment 15, into the bottom of a collection vessel 16. A gas inlet 33 provides for fluidisation of the catalyst in the collection vessel 16. Catalyst fines are recovered from the gaseous product by a cyclonic separator 18 and the fines are returned to the collector vessel 16. The product output from the cyclonic separator at line 19, such as including lower olefins, is recovered and processed further (not shown). A portion of the catalyst is diverted from the collection vessel 16 to a regenerator 39 via a conduit 40 and returned to the collection vessel 16 via a conduit 43. A valve 41 on the conduit 40 provides for control of the catalyst sent to the regenerator 39 and a valve 42 on the conduit 43 provides for control of the catalyst return from the regenerator 39.

Accumulated (fluidised) catalyst C is shown in the collector vessel 16, and also shown in the stage vessels 28, 17.

In this embodiment having three riser sections, fluidised catalyst is added to the riser reactor system 10 not only at the bottom of the first riser 13 but also at the bottom of the second 14 and third 15 riser reactors. Standpipe 37 provides fluid communication between the collector vessel 16 and the bottom of the third riser segment 15 for this purpose. This standpipe is less than 20 meters high, so that a simple design with a single valve 38 suffices. Standpipe 30 connects the fluidized bed 28b in stage vessel 28 to the bottom of the second riser 14. The combination of conduit 29, stage vessel 28 and conduit 32 with the valves 32 and 36 represents an embodiment of a catalyst return apparatus according to the invention in itself.

Valves 38 and 32 are provided on the conduits 37, 30 respectively to control the flow of fluidised catalyst into the riser reactor system 10 at these points.

Each of the conduits 23, 27, 29, 37 has a height of 20 m or less, in particular a length of 20 m or less.

It will be understood that simpler embodiments of the present invention are obtained in case the riser reactor system only contains a single tall riser instead of the three segments shown. At the same overall height, the conduits 30 and 37 are not required then.

The system can also be simplified by not including the stage vessels 28 and 17 as well as the lines 22 and 44 as well as 34,35. If further only a single tall riser was present, the catalyst return apparatus would be formed by the conduits 23, 27 and 29 with the valves 26, 31, 26, which conduits would be in direct fluid communication with each other then. Depending on the total height, the one of the valves could even be omitted.

The present invention has been discussed in the context of an oxygenate-to-olefins reactor system. It will however be clear that the invention can also be used in riser reactor systems for other processes, including other chemical processes, and refinery processes such as fluidized catalytic cracking.

What is claimed is:

1. A catalyst return apparatus suitable for use in a riser reactor system, the apparatus comprising a catalyst return conduit and at least two flow control devices in series along the catalyst return conduit and at least two means to reconstitute catalyst flow, excluding regeneration and heat exchange units, in series along the catalyst return conduit, wherein the length of the catalyst return conduit is more than 20 m.

2. An apparatus as claimed in claim 1, wherein the length of the catalyst return conduit is more than 30 m.

3. An apparatus as claimed in claim 1, wherein the means to reconstitute catalyst flow comprises at least one stage vessel, wherein the at least one stage vessel has a width at least twice a width of the conduit.

4. An apparatus as claimed in claim 1, wherein the means to reconstitute catalyst flow comprises a gas inlet to further fluidise catalyst particles during use.

5. An apparatus as claimed in claim 1, wherein the catalyst return conduit comprises at least one means to reconstitute catalyst flow at least every 20 m.

6. An apparatus as claimed in claim 1, wherein at least one flow control device is provided for each means to reconstitute catalyst flow, within 2 m upstream thereof, to control the fluid within the conduit at that point.

7. An apparatus as claimed in claim 1, wherein the conduit comprises a first portion above the means to reconstitute catalyst flow and a second portion below the means to reconstitute catalyst flow, wherein the first and second portions are not co-linear.

* * * * *